(12) United States Patent
Teichmann

(10) Patent No.: US 8,659,386 B2
(45) Date of Patent: Feb. 25, 2014

(54) CODING OF LASER FIBERS

(75) Inventor: Heinrich-Otto Teichmann, Bovenden (DE)

(73) Assignee: Lisa Laser Products OHG Fuhrberg & Teichmann, Katlenburg-Lindau (DE)

( * ) Notice: Subject to any disclaimer, the term of this patent is extended or adjusted under 35 U.S.C. 154(b) by 1202 days.

(21) Appl. No.: 12/062,011

(22) Filed: Apr. 3, 2008

(65) Prior Publication Data

US 2008/0246582 A1    Oct. 9, 2008

(30) Foreign Application Priority Data

Apr. 5, 2007    (DE) .......................... 10 2007 016 942

(51) Int. Cl.
*G05B 19/00* (2006.01)
*H04B 10/00* (2013.01)
*G07C 11/00* (2006.01)

(52) U.S. Cl.
USPC ............................. 340/5.1; 340/10.1; 235/385

(58) Field of Classification Search
CPC .......... G07C 11/00; H01S 3/10; A61B 18/22; A61F 9/008
USPC ............ 340/5.1, 10.1; 398/140; 372/38.02, 8; 606/16; 385/134, 77, 147; 235/385
See application file for complete search history.

(56) References Cited

U.S. PATENT DOCUMENTS

| | | | | |
|---|---|---|---|---|
| 5,400,267 A * | 3/1995 | Denen et al. | ..................... | 702/59 |
| 5,848,209 A * | 12/1998 | Evans et al. | ..................... | 385/88 |
| 7,194,180 B2 * | 3/2007 | Becker | .......................... | 385/134 |
| 7,483,457 B2 * | 1/2009 | Howe et al. | ................. | 372/38.02 |
| 7,568,619 B2 * | 8/2009 | Todd et al. | ..................... | 235/385 |
| 7,837,091 B2 * | 11/2010 | Cook et al. | ..................... | 235/375 |
| 2004/0073202 A1 | 4/2004 | Illich et al. | | |
| 2006/0089629 A1 | 4/2006 | Howe et al. | | |

FOREIGN PATENT DOCUMENTS

| | | |
|---|---|---|
| DE | 10236175 A1 | 2/2004 |
| DE | 60303812 T2 | 11/2006 |
| WO | WO 2006/127526 A2 | 11/2006 |

* cited by examiner

*Primary Examiner* — Nam V Nguyen
(74) *Attorney, Agent, or Firm* — Thomas | Horstemeyer, LLP

(57) ABSTRACT

For operating a laser device to which an identification code is assigned in combination with a laser fiber depending on an identification code assigned to the laser fiber, the identification code assigned to the laser fiber is generated depending on the identification code of the laser device and compared by the laser device with its own identification code in such a way that the laser fiber may only be used in combination with the particular laser device.

12 Claims, 1 Drawing Sheet

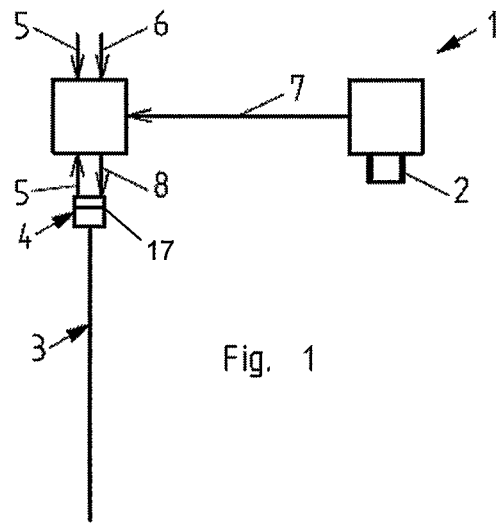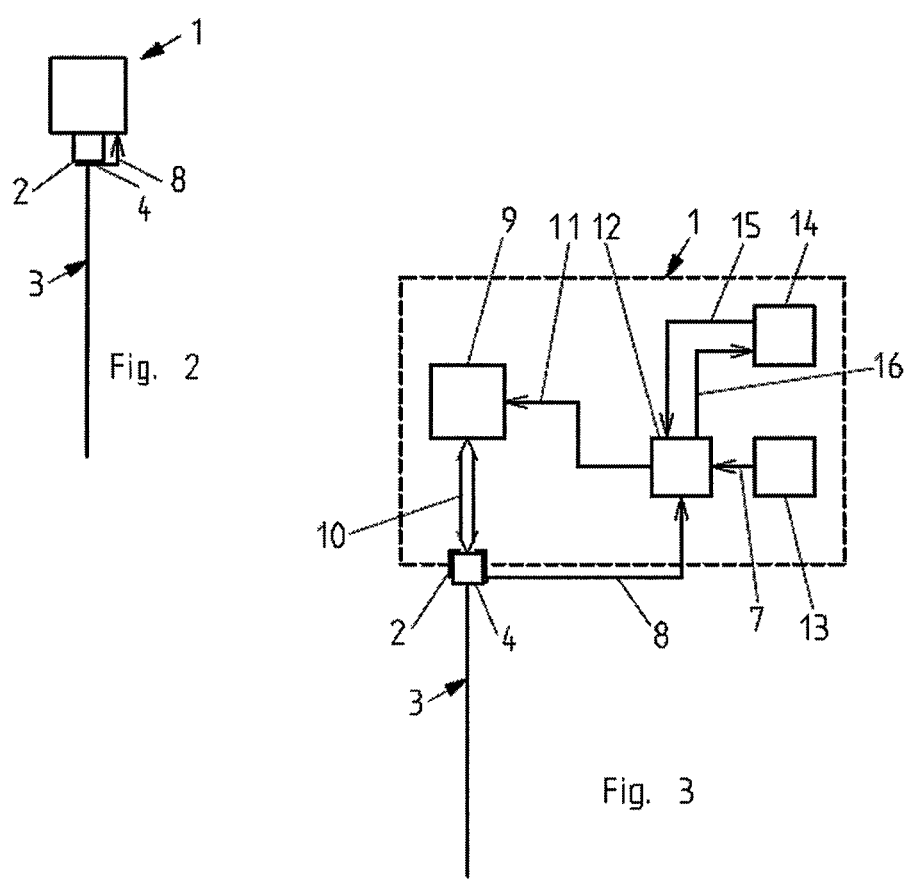

CODING OF LASER FIBERS

CROSS REFERENCE TO RELATED APPLICATIONS

This application claims priority to co-pending German Patent Application No. DE 10 2007 016 942.8 filed Apr. 5, 2007 and entitled "Codierung von Laserfasern".

FIELD OF THE INVENTION

The invention relates to a laser system comprising a laser fiber having a connector; and a laser device having a laser for supplying laser light, a coupler for the connector of the laser fiber for coupling laser light in the laser fiber connected to the coupler via its connector, and a controller for operating the laser depending on an identification code assigned to the laser fiber.

Further, the present invention relates to a method of operating a laser device to which an identification code is assigned in combination with a laser fiber depending on an identification code assigned to the laser fiber.

The term laser fiber is intended to be understood as any light guide made according to fiber or waveguide technology which is suitable for guiding laser light. Particularly the invention in related to such laser fibers or waveguides which are used to transfer laser light for medical applications.

DESCRIPTION OF RELATED ART

A laser system and a method of operating a laser device in which an identification code is assigned to a laser fiber are known from US 2006/0089629 A1. Here, the identification code assigned to the laser is stored in a read and write memory device connected to the laser fiber, which, for example, is an RFID-device or a so-called transponder. A controller of the laser device reads the identification code from the read and write memory device and, based on this identification code, checks whether the laser fiber is still useable or whether a predetermined maximum duration of use has already been exceeded. Depending on the result of this check the laser of the laser device is operated. At the end of the present use, the controller of the laser device writes an amended identification code in the read and write memory device of the laser fiber to record the wear due to the use of the laser fiber. In a new use of the laser fiber, the controller then reads the amended identification code and only operates the laser, if a maximum duration of use of the laser fiber, after which its function can no longer be ensured, has not yet been exceeded. In addition to the remainder of the permissible duration of use, the identification code of the laser fiber may also include information on a use-by date, the absolute age and/or the model of the laser fiber, and/or the applicable energy, frequency and power settings to be applied in using the laser fiber.

The known laser device and the known method are associated with the potential danger that used-up laser fibers are manipulated, and that they are thus used far beyond their permissible duration of use. There also is a danger that unauthorized laser fibers are used in combination with the laser device in that these unauthorized laser fibers are provided with a read and write memory device in which an identification code of an unused laser fiber is stored. Such a read and write memory device could also be provided independently of a laser fiber to de-block and use any laser fibers. In addition, a long term documentation of the use of a particular laser fiber is dependent on that the laser fiber is kept save, even after the expiry of its complete permissible duration of use.

A laser system and a method of operating a laser system in which a read and write memory device is associated to a laser fiber but not connected to the laser fiber, on the one hand, and in which the laser fiber is permanently connected with an identifier which is automatically read-in upon the laser fiber being coupled to the laser device, on the other hand, is known from WO 2006/127526 A2. The laser device both reads the identification code from the read and write memory device and the identifier of the laser fiber coupled thereto, and checks on this basis whether the laser fiber fits to the read and write memory device. A controller of the laser device records the use of the laser fiber on the read and write memory device.

The disadvantages of this known laser system and this known method of operating a laser device are in general the same as those of the previously described prior art, except of that it is sufficient for documentation keep the separate read and write memory device instead of the complete laser fiber.

A further laser system comprising a laser device and a method of operating a laser device are known from US 2004/0073202 A1. The laser system comprises a hand-held unit coupled to a distal end of laser fiber which is coupled to the laser device at its proximal end. The hand-held unit comprises a data sending device sending data as optical signals via the laser fiber to a controller of the laser device. These data, for example, include data related to any devices connected to the hand-held unit, which are automatically read-in at the hand-held unit and used for operating the laser device.

There remains a need for a laser system comprising a laser device and a method of operating a laser device which generally prevent external manipulations of already expired laser fibers and use of faked laser fibers.

SUMMARY OF THE INVENTION

In its first aspect the present invention provides a laser system comprising: a laser fiber having a connector; and a laser device having a laser for supplying laser light, a coupler for the connector of the laser fiber for coupling laser light in the laser fiber connected to the coupler via its connector, and a controller for operating the laser depending on an identification code assigned to the laser fiber, wherein the controller compares the identification code assigned to the laser fiber with an identification code assigned to the individual laser device and only operates the laser, if the comparison has the outcome that the laser fiber is exclusively intended for the particular laser device.

In its second aspect the present invention provides a method of operating a laser device to which an identification code is assigned in combination with a laser fiber depending on an identification code assigned to the laser fiber, wherein the identification code assigned to the laser fiber is generated depending on the identification code assigned to the laser device, and wherein, prior to operating the laser device in combination with the laser fiber, the identification code assigned to the laser fiber is compared to the identification code assigned to the laser device in such a way that the laser fiber may only be used in combination with that particular laser device to which the identification code is assigned depending on the basis of which the identification code of the laser fiber has been generated.

In the laser system according to the present invention, the controller of the laser device compares an identification code assigned to the laser fiber with an identification code assigned to the individual laser device, and only authorizes or de-blocks the laser, if this comparison has the outcome that the laser fibers is exclusively destined for the individual laser device. I.e. a particular laser fiber may only be used with a particular laser device. This provision alone makes manipulations much more difficult, as these manipulations have to be individualized with regard to the particular laser device to be successful.

It will be appreciated that the identification code of the laser may be designed by those skilled in the art according to known methods in such a way that it can not be generated by an unauthorized person, even if the identification code of the laser device is known. Whereas the identification code of the laser device as such is preferably permanently programmed in the control of the laser device but freely accessible, the algorithm according to which the controller of the laser device compares the identification code of the laser fiber with the identification code of the laser device is secret, i.e. can not be read out of the controller.

As the identification code of the laser fiber may not be kept secret, an input device may be provided for entering the identification code of the laser fiber in the controller, which allows for manually entering the identification code by means of a keyboard, for example, a keyboard only comprising figure keys being sufficient.

The laser device may, however, also comprise a reading device for reading the identification code of the laser fiber from a data carrier. This reading device may, for example, be a barcode scanner in which a card which carries the identification code of the laser fiber in form of a barcode is inserted as the data carrier.

It is also possible that the reading device is incorporated in the coupler for the laser fiber at the laser device and automatically reads a data carrier located at the laser fiber. Here, the data carrier may for example be a chip located in or close to the connector of the laser fiber, which is read out via electric contacts provided at the coupler; the data carrier may also be a so-called transponder or the like which may even be arranged remote of the coupler.

The data carrier may be a read and write data carrier. The laser device, however, does only read the identification code and does not manipulate the data on the data carrier. A record of use of the laser fiber is kept in the controller of the laser device and is assigned to the identification code. I.e. the record of use is written in the laser device and stored therein. The record of use may be kept like an account into which a starting value is written depending on the identification code of the laser fiber and to which a value corresponding to each single use of the laser fiber is debited until the account balance is zero when the laser fiber is used-up. Then the controller stops any further use of the laser device in combination with the laser fiber despite the fact that the laser fiber generally fits to the laser device due to its identification code. The record of use only kept in the controller prevents manipulations from outside to de-block used-up or faked laser fibers by manipulating their identification code or generating a faked identification code. A second laser fiber having the same identification code could, due to its identification code, only be used with the same laser device; in this laser device, however, it is stored that the laser fiber with this particular identification code is already used-up. Thus, the identification code of the laser fiber as such has been used-up.

Further, reading the record of use from the controller of the laser device allows to inspect with which laser fibers the laser device has been used and whether these laser fibers include unauthorized ones.

According to the new method of operating a laser device the identification code of the laser fiber is generated depending on the identification code of the laser device, and the identification code of the laser fiber is compared with the identification code of the laser device prior to the operation of the laser device in combination with the laser fiber in such a way that the laser fiber is only useable in combination with that particular laser device for which its identification code has been generated. It is to be understood, that the algorithm according to which the identification code of the laser fiber is generated based on the identification code of the laser device has to be kept as secret as the algorithm according to which the identification code of the laser fiber is compared to the identification code of the laser device.

The identification code as such, however, may for example be printed on a label of the laser fiber, this label being directly attached to the laser fiber or to its packaging.

Alternatively or additionally, the identification code may be written into a read and write data carrier of the laser fiber. This read and write data carrier may also be directly connected to the laser fiber or only be supplied together with the laser fiber. In both cases it is possible, that the identification code is automatically read-in from the read and write data carrier of the laser fiber by the controller of the laser device upon connecting the laser fiber to the laser device.

It is appreciated that it is beneficial, if the identification code of the laser fiber is not only generated depending on the identification code of the laser fiber but also depending on the properties of the laser fiber so that information on the properties of the laser fiber can be transferred to the controller of the laser device together with the identification code. The type of laser fiber, its technical data, including their maximum duration of use and a use-by date of the laser fiber may belong to the relevant properties of the laser fiber. In the same way, the permissible operation parameters of the laser fiber like energy, frequency and power may be incorporate into the identification code.

As already indicated with regard to the new laser system it is particularly preferred, if a record of use is kept in the laser device with regard to each identification code read-in or entered. This record of use may primary serve for preventing a further use of the laser device with the same laser fiber after a maximum duration of use of the laser fiber has been recorded. The record of use may also be used for later evaluations, without any necessity of keeping the record separately. It is appreciated, that the maximum duration of use from which on any further use of the laser device with the same laser fiber is stopped will—as a rule—depend on the type of the laser fiber which may be read-in by the laser device with the identification code of the laser fiber. Additionally, the maximum duration of use may be independently reached due to different criteria. The lapse of time since the first use, the absolute duration of use, the number of separate uses and the total amount of energy coupled into the laser fiber may belong to these criteria.

BRIEF DESCRIPTION OF THE DRAWINGS

Other features and advantages of the present invention will become apparent to one with skill in the art upon examination of the following drawings and the detailed description. It is intended that all such additional features and advantages be included herein within the scope of the present invention, as defined by the claims, which follow.

FIG. 1 schematically illustrates the generation of an identification code of a laser fiber as a step of the new method.

FIG. 2 indicates the direction of data transfer between a laser fiber and a laser device, to which the laser fiber is connected; and FIG. 3 sketches the function of a controller of the laser device in operating the laser fiber.

DETAILED DESCRIPTION

A detailed description of embodiments of the present invention is provided with reference to FIG. 1 to 3.

FIG. 1 schematically shows a laser system including a laser device 1 having a coupler 2 for a laser fiber, and a laser fiber 3 provided for being coupled to the laser device 1 and having a connector 4 fitting to the coupler 2. A read and write data carrier 17 is incorporated into the connector 4 of the laser fiber 3. This read and write data carrier may contain information 5 related, for example, to the model of the laser fiber 3 and its properties, the permissible operation parameters as well as the production date of the laser fiber 3 and a use-by date which may be derived from the former information. This information may be read out by a coding device 6 from the read and write data carrier located 17 in the connector 4. The coding device 6 may, however, receive this information 5 from another source not depicted here. From the laser device 1 the coding device 6 receives an identification code 7 assigned to the laser device 1 as a further input information. Using a coding algorithm, the coding device 6 generates an identification code 8 for the laser fiber 3 based on the information 5 and the identification code 7 of the laser device 1. The coding device 6 writes this identification code 8 in the read and write data carrier 17 included in the connector 4. The coding algorithm according to which the identification code 8 is generated based on the identification code 7 and the information 5 is to be kept secret, whereas both the identification code 7 and the identification code 8 and the information 5 may be freely accessible. The coding device 6 is for example used in a manufacturing plant in which the laser fiber 3 is produced or prepared. In this case, the information 5 is usually supplied by another source than the laser fiber 3 itself and may be stored together with the identification code in the read and write data carrier 17. The coding device 6 may also be used by a reseller, who provides laser fibers 3 from a stock with an identification code 8 for use with a particular laser device 1 individualized by the identification code 7.

FIG. 2 shows the laser fiber 3 with its connector 4 inserted into the coupler 2 of the laser device 1. The laser device 1 reads the identification code 8 from the connector 4 or the read and write data carrier located therein, and compares this identification code 8 with its stored identification code 7 prior to coupling laser light into the laser fiber 3.

FIG. 3 shows the parts of the laser device 1 and the steps executed in the laser device 1 which are essential for the present invention. The laser device 1 comprises a laser 9 for coupling laser light 10 into the laser fiber 3 connected to the coupler 2 via its connector 4. The laser 9 is controlled via control signals 11 from a controller 12. The controller 12 reads the identification code 8 of the laser fiber 3 in that it for example queries the read and write data carrier located in the connector 4 and having the form of a transponder. Based on an algorithm which also has to be kept secret, the controller 12 compares the identification code 8 with the identification code 7 which is permanently programmed into a memory 13. Based on this comparison the controller 12 determines whether the laser fiber 3 is intended for use with the present laser device 1 so that the laser 9 may be activated in general. Additionally, the controller 12 queries a further memory 14 in which records of use 15 are kept for all laser fibers 3 the identification codes 8 of which have already been read-in by the controller 12. From the records of use 15 the controller 12 determines whether the actual laser fiber 3 has already been used-up, for example, due to a number of already occurred single uses or a period of time elapsed since its first use, or a maximum total duration of use, or a maximum amount energy coupled-in so that it is not suitable for further uses. In this case, the laser 9 is not activated by the operation signal 11. No activation also occurs, if an absolute use-by date of the laser fiber 3 included in the identification code 8 is exceeded. In all other cases, the laser 9 is activated by the operation signal 11, and the laser couples laser light 10 in the laser fiber 3. The controller 12 keeps a record of this use of the laser fiber 3 in that it writes use data 16 in the memory 17 to continue the record of use 15.

The identification code 7 may be supplied by the user of the laser device 1 when ordering a laser fiber 3 for the laser device 1 orally, in writing or digitally. Similarly, the identification code 8 of the laser fiber 3 may be transmitted in various ways. It may be printed as a simple figure on the packaging of the laser fiber 3, and entered in the laser device 1 by the user via a keypad (nor depicted here). The laser device 1 may also have a barcode scanner (also not depicted here) via which a barcode coding the identification code 8 may be read. Such a barcode can be provided on the laser fiber 3, its connector 4 or on a label attached thereto, or on a separate card or even on the packaging of the laser fiber 3. The read and write data carrier which has been described previously does also not have to be a part of the laser fiber 3, and it is only one of a number possible embodiments with regard to transmitting the identification code 8 to the laser device 1 which are obvious to those skilled in the art.

Many variations and modifications may be made to the preferred embodiments of the invention without departing substantially from the spirit and principles of the invention. All such modifications and variations are intended to be included herein within the scope of the present invention, as defined by the following claims.

List of Reference Numerals 1 laser device
2 coupler
3 laser fiber
4 connector
5 information
6 coding device
7 identification code
8 identification code
9 laser
10 laser light
11 control signal
12 controller
13 memory
14 memory
15 record of use
16 use data
17 data carrier

What I claim is:

1. A laser system comprising:
a laser fiber having a connector; and
a laser device having
  a laser for supplying laser light,
  a coupler for the connector of the laser fiber for coupling laser light in the laser fiber connected to the coupler via its connector, and
  a controller for operating the laser depending on an identification code assigned to the laser fiber, wherein the controller compares the identification code assigned to the laser fiber with an identification code assigned to the laser device, wherein the identification code assigned to the laser device is different from identification codes assigned to other laser devices, wherein the identification code assigned to the laser device is permanently programmed into a memory of the laser device, wherein the comparison is made according to a secret algorithm stored in the laser device, and the controller only operates the laser, if the comparison has the outcome that the laser fiber is exclusively intended for the laser device and not any of the other laser devices, wherein the controller stores in the laser device a record of use of each laser fiber used in combination with the laser device under the identification code assigned to the laser fiber.

2. The laser system according to claim 1, wherein the identification code assigned to the laser device is permanently programmed in the laser device.

3. The laser system according to claim 1, wherein the controller has an input device for manually inputting the identification code of the laser fiber in the controller.

4. The laser system according to claim 1, wherein the controller automatically reads the identification code assigned to the laser fiber from a data carrier.

5. The laser system according to claim 4, wherein the controller automatically reads the identification code assigned to that laser fiber which is presently connected to the coupler for the laser fiber.

6. The laser system of claim 1, wherein the controller prevents a further use of the laser device in combination with a particular laser fiber, if the record of use indicates that a predetermined maximum use of the particular laser fiber has already been reached.

7. A method of operating a laser device to which an identification code is assigned in combination with a laser fiber depending on an identification code assigned to the laser fiber, wherein the identification code assigned to the laser fiber is generated depending on the identification code assigned to the laser device, wherein the identification code assigned to the laser device is permanently programmed into a memory of the laser device, wherein a controller stores in the laser device a record of use of the laser fiber used in combination with the laser device under the identification code assigned to the laser fiber, and wherein, prior to operating the laser device in combination with the laser fiber, the identification code assigned to the laser fiber is compared to the identification code assigned to the laser device in such a way that the laser fiber may only be used in combination with the laser device to which the identification code is assigned depending on the basis of which the identification code of the laser fiber has been generated, wherein the comparison is made according to a secret algorithm stored in the laser device, and other laser devices are assigned other identification codes that are different from the identification code of the laser device.

8. The method of claim 7, wherein the identification code assigned to the laser fiber is printed on a label of the laser fiber.

9. The method of claim 7, wherein the identification code assigned to the laser fiber is written in a read and write data carrier of the laser fiber.

10. The method of claim 9, wherein the identification code assigned to the laser fiber is automatically read from the read and write data carrier of the laser fiber by the laser device.

11. The method of claim 7, wherein the identification code assigned to the laser fiber is generated also depending on properties of the laser fiber.

12. The method of claim 7, wherein a further use of the laser device in combination with a particular laser fiber is prevented, if the record of use indicates that a predetermined maximum use of the particular laser fiber has already been reached.

* * * * *